(12) United States Patent
Baraldi et al.

(10) Patent No.: US 7,785,284 B2
(45) Date of Patent: Aug. 31, 2010

(54) JOINT FOR FLUID TRANSPORT LINES FOR MEDICAL USE

(75) Inventors: Vincenzo Baraldi, Quistello (IT); Annalisa Delnevo, Sant'Agata Bolognese (IT); Gianfranco Marchesi, Camposanto (IT); Andrea Ligabue, San Prospero (IT); Massimo Zaccarelli, San Felice sul Panaro (IT)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 11/898,014

(22) Filed: Sep. 7, 2007

(65) Prior Publication Data

US 2008/0004562 A1 Jan. 3, 2008

Related U.S. Application Data

(62) Division of application No. 10/859,546, filed on Jun. 3, 2004, now Pat. No. 7,291,123.

(60) Provisional application No. 60/511,327, filed on Oct. 16, 2003.

(30) Foreign Application Priority Data

Jun. 4, 2003 (IT) .......................... MO2003A0165

(51) Int. Cl.
*A61M 37/00* (2006.01)

(52) U.S. Cl. ....................... 604/6.16; 604/4.01; 604/6.1; 604/6.11; 604/6.08; 604/533; 439/5; 439/87; 210/233; 327/29; 327/33; 327/34; 327/37; 327/40; 327/41; 327/42; 327/43; 327/44; 327/45; 327/46; 327/47; 327/169; 327/379; 327/549; 327/552; 327/553; 327/554; 327/555; 327/603; 327/317; 403/32

(58) Field of Classification Search ................. 604/6.16, 604/4.01, 6.1, 6.11, 6.08, 533; 439/5, 87; 327/29, 33, 34, 37, 40, 41–47, 169, 317, 327/379, 549, 551–555, 603; 403/32; 210/233
See application file for complete search history.

(56) References Cited

U.S. PATENT DOCUMENTS 3,070,132 A 12/1962 Sheridan (Continued)

FOREIGN PATENT DOCUMENTS

EP 0 488 410 A1 6/1992

(Continued)

*Primary Examiner*—Tatyana Zalukaeva
*Assistant Examiner*—Ginger T Chapman
(74) *Attorney, Agent, or Firm*—Finnegan, Henderson, Farabow, Garrett & Dunner LLP

(57) ABSTRACT

The joint (36) comprises a tubular body (37) having two connecting zones (38, 39) each connected by an end to a tubular element (40) of a fluid transport line, giving continuity to passage of fluid. The tubular body is made of a mixture of an electrically-conductive material such as PVC, with carbon black to give it electrical conductivity. The joint has an internal surface (41) which is destined to come into contact with the transported fluid, and an external surface which is destined to have a grounded galvanic contact. The joint is inserted in the discharge fluid drainage line of a dialyzer filter, in an apparatus for intensive treatment of acute renal insufficiency, for eliminating ECG artefacts due to functioning of peristaltic pumps in the apparatus.

30 Claims, 6 Drawing Sheets

U.S. PATENT DOCUMENTS

| | | | |
|---|---|---|---|
| 3,580,983 A | 5/1971 | Jackson | |
| 3,914,002 A | 10/1975 | Berliner et al. | |
| 4,012,103 A | 3/1977 | Lunquist | |
| 4,027,659 A | 6/1977 | Slingluff | |
| 4,059,847 A | 11/1977 | Phillips et al. | |
| 4,215,384 A | 7/1980 | Elson | |
| 4,537,200 A | 8/1985 | Widrow | |
| 4,640,563 A | 2/1987 | LeBlanc | |
| 4,675,780 A * | 6/1987 | Barnes et al. | 361/215 |
| 4,983,456 A * | 1/1991 | Iwaskow et al. | 442/229 |
| 5,127,907 A | 7/1992 | Coutré et al. | |
| 5,220,920 A | 6/1993 | Gharib | |
| 5,284,151 A | 2/1994 | Onoda | |
| 5,305,760 A | 4/1994 | McKown et al. | |
| 5,387,196 A * | 2/1995 | Green et al. | 604/158 |
| 5,431,638 A * | 7/1995 | Hennig et al. | 604/264 |
| 5,618,309 A | 4/1997 | Green et al. | |
| 5,754,388 A * | 5/1998 | Schmidt | 361/215 |
| 6,102,897 A | 8/2000 | Lang | |
| 6,287,484 B1 | 9/2001 | Hausslein et al. | |
| 6,497,841 B1 * | 12/2002 | Plotkin et al. | 422/46 |
| 2003/0036719 A1 | 2/2003 | Giacomelli et al. | |
| 2004/0225225 A1 | 11/2004 | Naumov et al. | |

FOREIGN PATENT DOCUMENTS

| | | |
|---|---|---|
| EP | 0 542 140 A2 | 5/1993 |
| EP | 0 542 140 A3 | 5/1993 |
| EP | 1424637 A1 | 6/2004 |
| FR | 2 547 504 | 12/1984 |
| GB | 1033971 | 6/1966 |
| JP | 5-237184 | 9/1993 |
| JP | 2003-47653 | 2/2003 |
| JP | 2003-518413 | 6/2003 |
| WO | WO01/47581 | 7/2001 |
| WO | WO 02/13689 A2 | 2/2002 |
| WO | WO 02/070041 A1 * | 9/2002 |

* cited by examiner

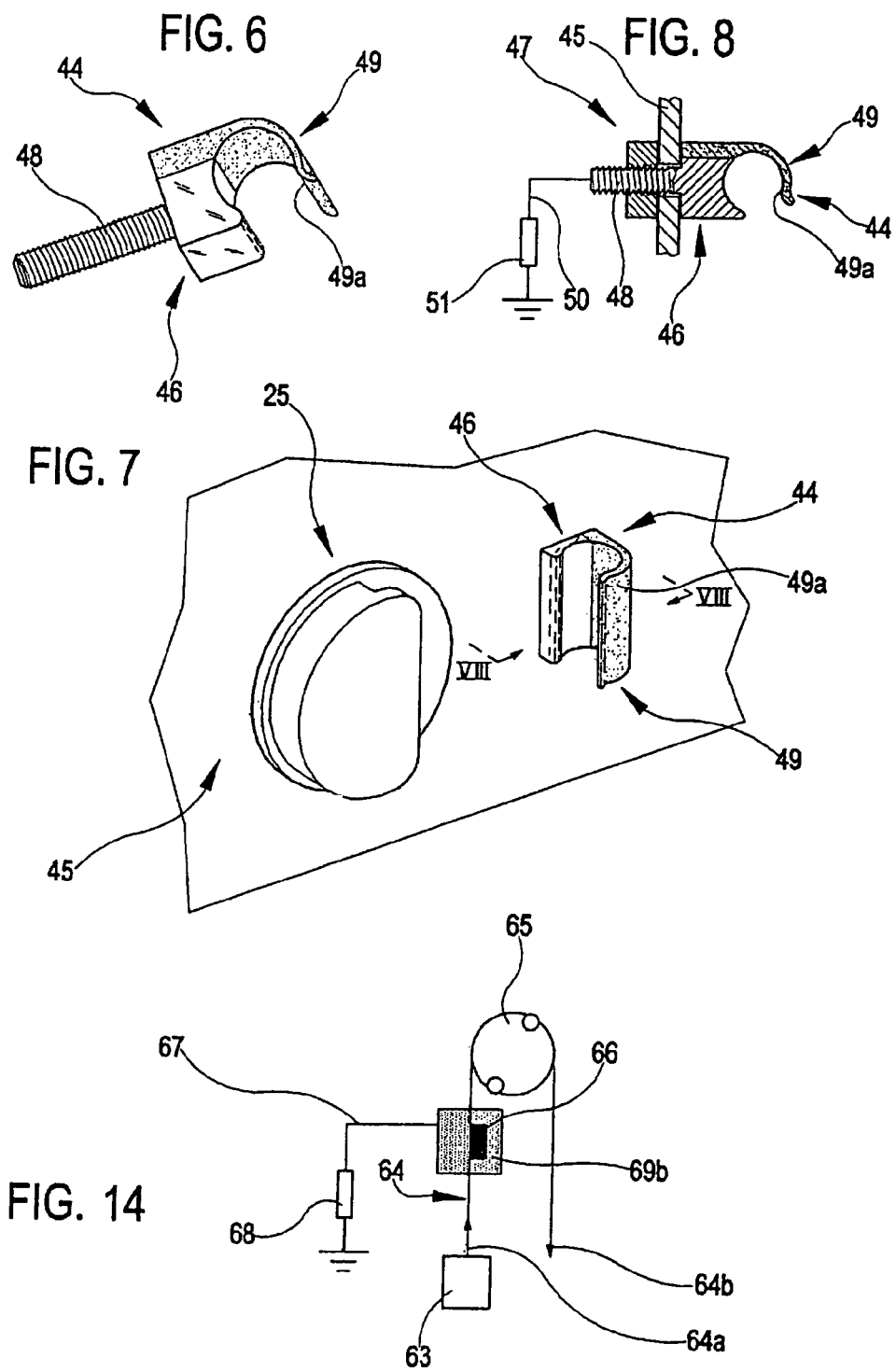

JOINT FOR FLUID TRANSPORT LINES FOR MEDICAL USE

This application is a divisional of U.S. patent application Ser. No. 10/859,546, filed Jun. 3, 2004, now U.S. Pat. No. 7,291,123 and claims the benefit of U.S. provisional application no. 60/511,327, filed Oct. 16, 2003, which is incorporated herein by reference.

BACKGROUND OF THE INVENTION

The invention relates to a joint for fluid transport lines for medical use, to a fluid transport line comprising the joint, to an infusion device comprising the line, to a circuit for extracorporeal blood treatment comprising the line, to a machine for extracorporeal blood treatment which is operatively associable to the circuit, and to an apparatus for extracorporeal treatment of blood comprising the machine and the circuit.

Specifically, though not exclusively, the invention can be usefully applied in the field of intensive treatment of acute renal insufficiency.

In the prior art, renal insufficiency, both chronic and acute, is treated by extracorporeal dialytic treatment, in which blood is removed from the patient through a withdrawal. line (arterial line) of an extracorporeal circuit, is sent to a first chamber (blood chamber) of a device for extracorporeal blood treatment (dialyzer or dialyzer filter, or artificial kidney), and is returned to the patient through a return line (venous line) of the extracorporeal circuit.

The treatment device comprises a second chamber (dialysis chamber) which is separated from the first by a semipermeable membrane. The second chamber has an outlet, fluidly connected to a drainage line for a discharge fluid, and generally also has an inlet, fluidly connected to a supply line of a fresh dialysis fluid.

In some treatments, especially in intensive therapy for treatment of acute renal insufficiency, one or more infusion lines can be provided, in particular a first infusion line, for supply of a first infusion fluid into the blood withdrawal line upstream of the dialyzer filter (pre-infusion), and a second infusion line, for supply of a second infusion fluid into the blood return line, downstream of the dialyzer filter (post-infusion).

To set up the treatment, the extracorporeal circuit is associated to a dialysis machine, which comprises at least one blood pump, in general a peristaltic pump, which is predisposed on the withdrawal line and is for the circulation of the blood. Usually the machine also comprises various other pumps, also usually peristaltic, for the circulation of the various fluids which flow in the other fluid transport lines: a drainage pump for circulating the discharge fluid along the drainage line; a pump for circulation of the fresh dialysis fluid along the supply line to the second chamber of the dialyzer filter; and an infusion pump for each infusion line.

Normally, during the course of extracorporeal treatment, some of the patient's physiological parameters are monitored, in particular it is usual to perform the patient's ECG.

One of the problems encountered during a dialysis treatment, especially in cases of intensive therapy, is that the rotation of the peristaltic pumps, in particular the blood pump, causes disturbances (known as artefacts) in the ECG.

This interference problem in the ECG is found both in complex apparatus, such as a dialysis machine for intensive treatment, as well as in more simple apparatus, such as an infusion device comprising an infusion line with a peristaltic pump.

The alteration in the ECG recording can lead to an indistinguishable tracing, or can cause distortions that might be wrongly interpreted and confused with signs of cardiac anomalies.

SUMMARY OF THE INVENTION

A main aim of the present invention is to provide a solution to the above-described problem existing in the prior art.

A further aim of the invention is to realize a fluid transport line that can be incorporable in a circuit for extracorporeal circulation of blood and/or medical fluids, thanks to which it is possible to eliminate ECG interference that can be traced to the operation of the machine associated to the circuit and which comprises means for circulation of the fluid in the circuit itself.

A further aim of the invention is to make available a machine for extracorporeal blood treatment, to which an extracorporeal circuit is operatively associable and which includes the above-cited fluid transport line, the functioning of which does not cause disturbances to the patient's ECG.

A further aim of the invention is to provide an infusion device, in which a medical infusion liquid is placed in circulation along an infusion line by a pump, thanks to which device it is possible to eliminate interferences which disturb the ECG and which are due to the operation of the pump.

An advantage of the invention is that it offers a simple and economical solution to the above-described problem of ECG artefacts caused by the operation of an apparatus for extracorporeal blood treatment.

A further advantage is that the invention realizes an apparatus for extracorporeal blood treatment which eliminates ECG artefacts and which at the same time responds to the necessary requisites of electrical insulation, thus eliminating any risks involving the patient's well-being.

A further advantage of the invention is that it provides a solution which does not lead to any problems relating to bio-compatibility.

A still further advantage of the invention is that it provides a fluid transport line, simple and economical to manufacture, which is easily produced using known production processes.

These aims and advantages and more besides are all attained by the present invention, as it is characterized in one or more of the appended claims.

Further characteristics and advantages of the invention will better emerge from the detailed description of at least one preferred but non-exclusive embodiment of the invention, made herein below with reference to the accompanying figures of the drawings, which are given by way of example and which are non-limiting.

BRIEF DESCRIPTION OF THE DRAWINGS

The description will be made with reference to the accompanying figures of the drawings, provided by way of non-limiting example, and in which:

FIG. 6 is a support element which is applicable to a front surface of a dialysis machine, and is provided for removable fastening of the joint of FIG. 2 or 4;

FIG. 7 shows the support element of FIG. 6 applied to the front surface of a dialysis machine;

FIG. 8 shows section VIII-VIII of FIG. 7;

FIG. 14 is a diagram of an infusion device made according to the present invention.

DETAILED DESCRIPTION

Figure 1:
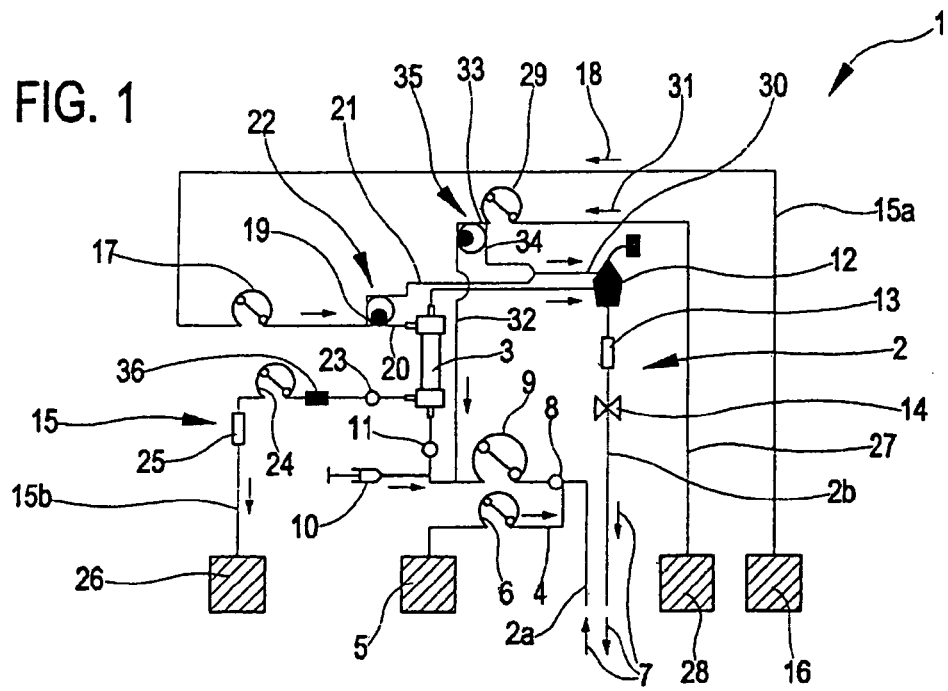
FIG. 1 is a diagram of a hydraulic circuit usable in a machine for intensive treatment according to the invention.

With reference to FIG. 1, the number 1 denotes an apparatus for extracorporeal treatment of blood, in particular a dialysis machine for intensive treatment.

A blood circuit 2 removes the blood from a patient, through a vascular access of known type and not illustrated, and, via at least one withdrawal line (inlet line or arterial line) 2a transports the blood, for example with continuous flow, to a blood treatment device 3 (or filtration unit, or dialyzer filter, or artificial kidney).

The blood crosses a first chamber (or blood chamber) of the blood treatment device 3 and, via a return line (or outlet line, or venous line) 2b, the treated blood is returned to the internal vascular system of the. patient.

The withdrawal line 2a is connected, immediately downstream of the blood withdrawal zone, to an auxiliary, pre-infusion line 4.

A source of secondary fluid 5 (for example a container or bag), supplies the pre-infusion line 4. The apparatus comprises means for moving the fluid, in the illustrated example constituted by an auxiliary pre-infusion pump 6 (for example a peristaltic pump), which means for moving the fluid control the flow of secondary fluid injected directly into the blood via the pre-infusion line 4.

The source of secondary fluid 5 can supply a suitable biological fluid to effect a pre-infusion, but can also supply an anti-coagulant.

The blood flows, in a blood circulation direction 7, from the withdrawal line 2a towards the filtration unit, and from the filtration unit flow via the return line 2b back to the patient.

A blood pressure sensor 8 is predisposed immediately downstream of the auxiliary pre-infusion line 4.

The apparatus comprises means for moving fluid, i.e. in the particular case at least one blood pump 9 for control and management of the blood flow in the blood circuit 2. The blood pump 9 is generally peristaltic.

A device 10 for administering an anti-coagulant, for example a syringe containing appropriate doses of heparin, operates on the withdrawal line 2a downstream of the blood pump 9.

The blood passes a further pressure sensor 11 which monitors. the correct flow into the blood circuit 2.

Then the blood enters the blood chamber of the treatment device 3, where, through a semi-permeable membrane, the desired substance, molecular and fluidic exchanges occur.

The treated blood, outletting from the treatment device 3, enters the return line 2b, crossing first a gas separator device (generally air) 12, predisposed to stop and expel any gassy substances or air bubbles present in the blood. The separator device 12 is operatively associated with a pressure sensor, of known type and not illustrated, for controlling the pressure in the return line 2b.

The treated blood outletting from the separator device 12 then crosses an air bubble sensor 13 which checks for absence of these dangerous formations internally of the treated blood.

Immediately downstream of the air bubble sensor 13 an intercept element 14 is located, the function of which is to block, during any alarms, the blood flow towards the patient.

Downstream of the intercept element 14 the treated blood is returned to the patient undergoing therapy.

A fluid circuit 15 is provided with at least one supply line 15a of a treatment fluid (fresh dialysis fluid), which enters a second chamber (dialysis chamber) of the treatment device 3, and a drainage line 15b outletting from the second chamber 3 of the device.

At least one source of treatment fluid 16 is connected to the supply line 15a of the fluid circuit 15 (the source of the treatment fluid 16 can be constituted, for example, by at least one bag containing a dialysis liquid).

The apparatus 1 comprises means for moving the fluid along the supply line 15a, including at least one supply pump 17 (in the illustrated embodiment a peristaltic pump), for controlling the flow of the treatment fluid coming from the source 16 and for defining a direction of circulation 18.

Downstream of the supply pump 17, along the circulation direction 18, there is a split 19 which divides the fluid circuit 15 into an injection branch 20 and an infusion branch 21. In particular the infusion branch 21 is connected to the return branch 2b of the blood circuit 2.

The infusion branch 21 enables a post-infusion directly into the blood circuit 2, using the treatment fluid coming from the source 16.

The injection branch 20 takes the treatment fluid directly to an inlet of the second chamber of the treatment device 3.

A selector switch 22 is predisposed in proximity of the split 19, and is for determining the percentage quantities of treatment fluid flow into the infusion branch 21 and into the injection branch 20. The selector switch 22, for example a cam switch or clamp switch, can assume at least a first operative configuration, in which the fluid is allowed to pass into the injection branch 20, and prevents passage into the infusion branch 21, and a second operative configuration, in which it allows passage into the infusion branch 21 and prevents passage into the injection branch 20. The selector switch 22 can modulate the quantities of fluid contemporaneously crossing one and the other branches 20 and 21, and can determine, including by programming, the changes in the quantities of fluids which flow in one branch or the other according to predetermined times and treatments.

The treatment fluid flowing in the injection branch 20 enters the second chamber (dialysis chamber) of the treatment device 3, which second chamber is separated from the first chamber (blood chamber) by the semi-permeable membrane which, as has already been mentioned, enables the correct substance exchanges between the blood and treatment fluid.

The fluid outletting from the second chamber of the treatment device 3, i.e. the discharge fluid, is transported by the drainage line 15b, also known as the effluent line.

A pressure sensor 23 is predisposed for controlling the functioning of the drainage line 15b.

Downstream of the pressure sensor 23 are located means for moving the fluid, for example a drainage pump 24, generally a peristaltic pump, able to control the flow in the drainage line 15b of the fluid circuit 15.

The discharge fluid crosses a blood leak detector 25 and is eliminated or directed into a container 26 for discharge fluid.

The apparatus comprises at least one further infusion line 27 which removes an infusion fluid from at least one auxiliary source 28 and, using means for moving fluid, usually a peristaltic infusion pump 29 which controls the flow, sends the fluid directly to the blood circuit 2 return line 2b. The infusion liquid can be introduced, as in the illustrated embodiment, directly into the gas separator device 12.

The infusion branch 21 of the fluid circuit 15 and the infusion line 27 are provided with a common end tract 30 for injection into the blood circuit 2. This end tract 30 is located downstream of the infusion pump 29 with respect to an infusion direction 14, and terminates directly in the separator device 12.

The infusion line 27 comprises at least one pre-infusion branch 32 connected to the withdrawal line 2a of the blood circuit 2. In more detail, downstream of the infusion pump 29 with respect to the infusion direction 31, there is a split 33 which divides the infusion line 27 into the pre-infusion branch 32 and a post-infusion branch 34. The pre-infusion branch 32 transports the infusion fluid, taken from the container 28, towards the withdrawal line 2a of the blood circuit 2, downstream of the blood pump 9 with respect to the circulation direction 7.

The post-infusion line. 34 is directly connected to the common end tract 30.

The infusion line 27 is provided with a selector switch 35, predisposed in proximity of the split 33, for determining the percentage quantity of the flow of liquid to be sent into the post-infusion branch 34 and the pre-infusion branch 32. The selector switch 35 can assume at least a first operative configuration, in which it allows passage of fluid into the pre-infusion branch 32 and prevents passage of fluid into the post-infusion branch 34, and at least a second operative configuration, in which it allows passage of fluid into the post-infusion branch 34 and prevents passage of fluid into the pre-infusion branch 32. The switch 35 can establish the percentage of fluid which must pass into each of the two branches 32 and 34, and can if necessary vary the times according to the treatments to be performed.

The apparatus 1 comprises a disposable part, usable in general for a single treatment, and a fixed part, which is used a number of times for various treatments on various patients. The fixed part is in effect the machine for extracorporeal blood treatment. The machine comprises, in general, a machine body which usually bears, on a front surface thereof, the various peristaltic pumps 6, 9, 17,. 24 and 29, and also the various sensors, denoted by 8, 11, 13, 23 and 25, and the means for controlling flow, denoted by 14, 22 and 35, and an interfacing system with the operator, which generally comprises a display for entering and reading data.

The machine body also bears, internally, all of the electronic control circuitry, including a machine command unit.

The disposable part comprises the treatment device 3 and the blood circuit 2; in the illustrated embodiment, in which the apparatus serves to perform dialysis treatment of the intensive kind, the disposable part also comprises the dialysis circuit 15.

Substantially the machine integrates all of. the instrumentation and apparatus destined to be used more than once, in various treatments, on one or more patients.

The disposable parts, destined to be used only once for each treatment to be performed on a patient, are borne on an integrated module, of known type and not illustrated, of the single-use type, applicable directly on the machine body.

The operation of the apparatus 1 includes a preliminary part, in which the disposable part is associated to the front surface of the machine body. During this phase the hydraulic circuit (blood circuit 2 and dialysis circuit 15) and the blood treatment circuit 3 are mounted on the machine in such a way that: the various peristaltic pumps engage the predisposed tracts of tubing (pump segments), which are generally U-shaped; all of the sensors are correctly engaged; and the containers of the various. fluids are fluidly coupled to the respective fluid transport lines.

After the blood circuit 2 has been connected, in a known way, to a vascular access of a patient, the blood pump 9 is started up, which starts circulation of the blood in the circuit.

Thereafter, according to the type of treatment to be performed, the machine for extracorporeal blood treatment is automatically started up and controlled by the command unit.

The apparatus for extracorporeal blood treatment described above is able to perform treatments, in particular intensive treatments, each of which comprises one or more of the following treatments, with predeterminable sequences: pure ultrafiltration, haemofiltration, haemodialysis, haemodiafiltration, plasma exchange.

In FIG. 1, 36 denotes a joint for fluid transport lines for medical use, which is made according to the object of the invention. The joint .36 is predisposed along the drainage line 15b immediately downstream of the blood treatment device 3, that is, just after the outlet from the second chamber of the device 3 and before the drainage pump 24. In the illustrated embodiment, the joint 36 is located between the pressure sensor 23 and the drainage pump 24. This joint 36 will be described in more detail herein below.

Figure 2:
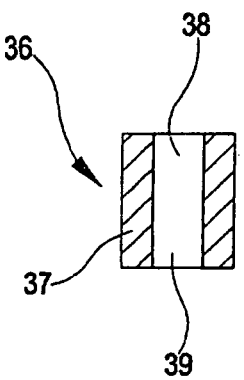
FIG. 2 is a longitudinal section of a joint for a fluid transport line realized according to the invention.
Figure 3:
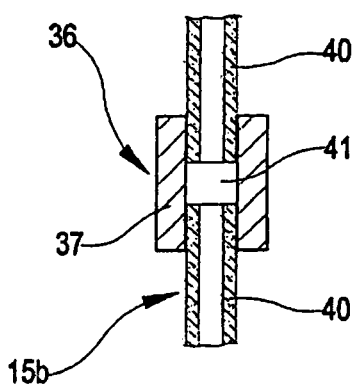
FIG. 3 shows the joint of FIG. 2 applied to a fluid transport line.

The joint 36 is illustrated, in a first embodiment, in FIG. 2. In FIG. 3, the joint 36 is coupled to the drainage line 15b.

The joint 36 comprises a tubular. body 37, substantially a sleeve-shape, having a cylindrical lateral external side and at two opposite ends two connecting zones 38 and 39, each of which has a cylindrical internal lateral surface for connecting with an end zone of a usual tubular element 40 of. a fluid transport line for medical use. The connection gives continuity to fluid passage.

Each tubular element 40 is a flexible elongate body, with elastically deformable walls, made of a dielectric plastic material, generally a thermoplastic resin, such as for example bio-compatible plasticized PVC.

The joint 36 is made in a single piece with a relatively small longitudinal extension having more rigid walls than the tubular elements 40.

In the illustrated example the joint 36 is made of a composite material including a mix of plastic material, generally a thermoplastic resin (for example the same material as the tubular elements 40, in this embodiment bio-compatible plasticized PVC), with at least one additive to give it electrical conductivity.

The combination of the above-mentioned additive with the thermoplastic resins, already dielectric, in suitable and known formulas, leads to obtaining a conductive material, though provided with relatively high electrical resistance.

The additive can be, for example, conductive carbon black, or another known product which, mixed with a thermoplastic. resin, transforms the latter from being an insulator to being a conductor.

In the illustrated embodiment, the material, obtained from a mixture of a plastic material and a conductor additive, can be extruded by usual processes and apparatus used for PVC.

In more detail, in the illustrated embodiment, the selected material for the conductive joint 36 is CABELEC® 3895, constituted by a compound including carbon black, plasticized PVC, stabilizer and lubricant.

The two connecting zones 38 and 39 of the joint are designed and structured to join the two tubular elements 40 solidly, one to another (even though axially distanced one from another), giving continuity to fluid passage. The two tubular elements 40, joined together by the joint 36, form a single conduit for the passage of a fluid.

The tubular body 37, made in a single piece, is produced by a plastic material pressing process.

The tubular body 37 is internally provided with at least one internal surface 41, destined to come into contact with the transported fluid, situated in an intermediate axial zone of the tubular body 37 comprised between the two end connecting zones 38 and 39.

The external surface of the tubular body 37 is destined to contact electrically with an element which is external of the fluid transport line, with the result that, via for example a grounded connection, the electrical currents present in the transported fluid transported in the fluid transport line can be dissipated. The external element, illustrated in figures from 6 to 8, will be better described herein below.

The tubular conductive joint 36, has a greater electrical conductivity than the tubular elements 40 which are reciprocally joined by the joint 36. The material of the tubular body 37 is, as has been mentioned, is based on a thermoplastic material, which in itself is dielectric, and which is made electrically conductive thanks to the addition, in the body of the plastic material, of carbon black or another suitable additive for obtaining electrical conductivity.

The joint 36 can therefore be considered an electrically conductive element, differently to the plastic tubular elements 40, which can be considered electric insulators.

The conductive joint 36 can be considered a high-resistance electrically-conductive element.

To achieve the desired aim, i.e. to considerably reduce or even eliminate disturbance of the ECG caused by electrostatic charges generated by the operation of peristaltic pumps, in particular the blood pump 9, the electrical impedance between the internal surface and the external surface of the tubular body 37 can vary within a range between 40 K$\Omega$ and 10 M$\Omega$. As will be more fully explained herein below, a substantial elimination of electrocardiograph disturbances has been verified, with the ECG connected up to a patient being subjected to extracorporeal treatment, using, in the apparatus, a conductive joint 36 having an electrical impedance variable between 200 K$\Omega$ and 2 M$\Omega$.

The material and conformation of the joint 36 simply and economically obtain a good, stable, resistant and well-sealed joint, between the jonit 36 and the tubular elements 40 which it joins. The joint union, permanently stable and unbreakable, can be obtained, during assembly, by a process of known type and already in use, for example, for solid connections by gluing of PVC tubes for medical products having corresponding plastic connectors. The procedure involves insertion of the end zones of the tubular elements 40 inside the connecting zones 38 and 39 of the joint 36, with a preliminary spreading on at least one of the coupling surfaces of a certain amount of a suitable glue, for example a cyclo-hexanone-based glue.

Figure 4:
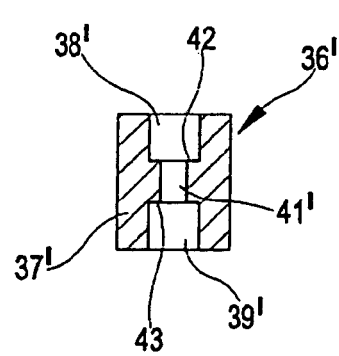
FIG. 4 is a second embodiment of a joint according to the present invention.
Figure 5:
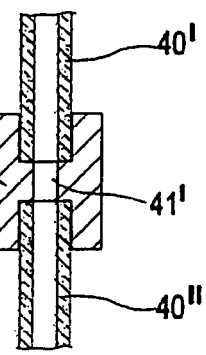
FIG. 5 is the joint of FIG. 4 applied to a fluid transport line.

In a second embodiment, illustrated in FIG. 4, the conductive joint 36' is constituted by a tubular body 37', made in a single piece, which internally comprises at least one first axial stop element 42, operatively associated to an end zone of a first tubular element 40', for limiting an axial insertion of the first tubular element within the tubular body.

In the illustrated embodiment, the tubular body 37' internally comprises a second axial stop element 43, axially distanced from the first axial stop element 42, and operatively associated to an end zone of the second tubular element 40", for limiting an axial insertion of the second tubular element inside the tubular body 37', in an opposite direction with respect to the axial insertion of the first tubular element 40'.

The tubular body 37' has an intermediate zone 41' comprised axially between the two end connecting zones 38' and 39', the internal diameter of which is smaller than the internal diameter of the connecting zones. The intermediate zone 41', with a smaller diameter, offers an inwardly-directed annular recess., axially delimited by two abutments, which form. the stop elements 42 and 43 which limit insertion of the end zones of the tubular elements 40' and 40". The elements 42 and 43 have the function of preventing total covering of the internal surface of the tubular body 37' by the tubular elements 40' and 40", so that a free intermediate zone 41' on the internal surface remains free, i.e. not covered by the end zones of the tubular elements 40' and 40" and in direct contact with the fluid which flows along the fluid transport line. This direct contact allows for dispersion to the outside of any electrostatic charges in the fluid.

The drainage line 15b of the apparatus 1 is an example of a fluid transport line, for medical use, made according to the invention.

The fluid transport line comprises at least a first part and a second part, both in contact with the transported fluid, in which the second part is made of a material having a greater electrical conductivity than the material the first part is made of. The second part of the line can comprise, as in the embodiment described herein, a conductive joint 36 or 36' like those first described, while the first part can comprise the tubular elements 40, 40', 40" described above.

The second part of line is also predisposed for galvanic connection to an element which is external of the line, as will be better explained herein below.

The conductive second part of the line exhibits at least one internal surface destined to contact with the transported fluid, and at least one external surface predisposed to be associated, in electrical contact, with a support element which is external of the line.

The first part is made of a thermoplastic material which is elastically deformable and dielectric, while the second part is made of a material composed of a mix of thermoplastic,. dielectric material with the addition of at least one additive which gives the mixture a certain electrical conductivity.

The additive also has the property of giving greater rigidity to the mixture.

The second part of the electrically conductive line is situated, with reference to the fluid transport direction, upstream of a pump segment of the line. The pump segment is a tract of line, normally U-shaped and elastically deformable, which is operatively associated to a normally-peristaltic pump, for circulation of the transported fluid.

The second part of electrically-conductive line can be located, in other embodiments which are not illustrated, in any other point of the hydraulic circuit of FIG. 1, either in the fluid circuit 15 (or dialysis circuit) or in the blood circuit 2.

The location on the drainage line 15b, immediately downstream of the treatment device 3, has the advantage of ensuring an efficient electrical connection between the second part of line (the joint 36) and the blood circuit 2, without resorting to direct contact between the blood and the second part of electrically-conductive line.

It has been found that the treatment device 3, or dialyzer filter, does not constitute a barrier to electrical communication between the blood circuit 2 and the fluid circuit 15.

This advantage can be found also in hydraulic circuits which are different from the one illustrated in FIG. 1: in particular, the use of the second conductive part of line is effective also in simplified hydraulic circuits, such as for example a circuit. for haemodiafiltration such as the one illustrated in FIG. 1, but lacking the branches 21 and 34, or a suitable circuit for effecting only haemofiltration, or a circuit suitable only for haemodialysis, or a circuit suitable only for pure ultrafiltration.

An apparatus for extracorporeal blood treatment, predisposed for cooperating with one of the above-cited hydraulic circuits, comprises at least one support element 44 predisposed to receive, with a mechanical engagement and in electrical contact, the above-mentioned second, electrically-conductive part of line (joint 36 or 36').

The support element 44 is solidly connected to a front panel 45 of the machine for extracorporeal blood treatment. An embodiment of this support element 44 is illustrated in FIG. 6, while FIGS. 7 and 8 show the same. support element 44 applied to the front panel 45 of the machine (in FIG. 7 the blood leak detector 25 can also be seen, located by the side of the support element 44).

The support element 44 comprises at least one electrically-conductive first part 46, made, for example, of metal, fixed to the front panel 45 of the machine by, for example, a screw connection 47. The conductive first part 46 can comprise a threaded stalk 48 for the screw connection with the front panel 45.

The support element 44 further comprises a second part 49, also dielectric and made of a plastic material, provided with a gripping organ 49a for removably fixing the fluid transport line to the conductive second part (the joint). The first and second parts 46 and 49 of the support element are solidly constrained one to another, for example by a screw connection (not illustrated).

The gripping organ 49a comprises, for example, a fastening, in the guise of an elastically deformable hook, which affords a seating in which the conductive joint 36 or 36' can be inserted and held tight in position. The joint 36 or 36' can be inserted and and removed manually from the seating.

The apparatus 1 further comprises a galvanic connection 50 which connects the support element 44 with an external mass, for external dissipation of any electrical charges present in the fluids, corporeal and/or medical, transported in the extracorporeal hydraulic circuit. The galvanic connection So terminates in the conductive first part 46 of the support element 44. In the illustrated embodiment the galvanic connection 50 is a true and proper earth for the joint 36, comprising at least one electrical earthing cable which connects the conductive first part of the support element, which is in contact with the above-mentioned conductive second part of line (joint 36 or 36'), with the machine body, which machine body is in turn normally provided with its own grounding.

The galvanic connection 50 also comprises at least one safety electrical impedance 51, of a predetermined entity, predisposed along the grounding cable between the support element 44 and the machine body. This safety impedance 51 guarantees the machine's electrical insulation, as required by the standards, together with the impedance value of the conductive joint 36 or 36'. The entity of the electrical impedance 51 can be, for example, above about 0.1 M$\Omega$. It has been found that an efficient elimination of ECG artefacts (caused by the action of the peristaltic pumps) is also achieved with a safety impedance 51 of above about 1.0 M$\Omega$. Alternatively to the use of a single impedance 51 of about 1.0 M$\Omega$, a plurality of electrical impedances, of predetermined entities (for. example each not below about 2.0 M$\Omega$), could be predisposed in parallel. along the galvanic connection, with the aim of reducing the power dissipated.

The galvanic connection to earth can comprise, for example., an electronic board having: one or more impedances having predefined characteristics, at least a first contact for connecting to the conductive part 46 of the support element, and at least a second contact for connecting to the earthing cable.

Figure 9:
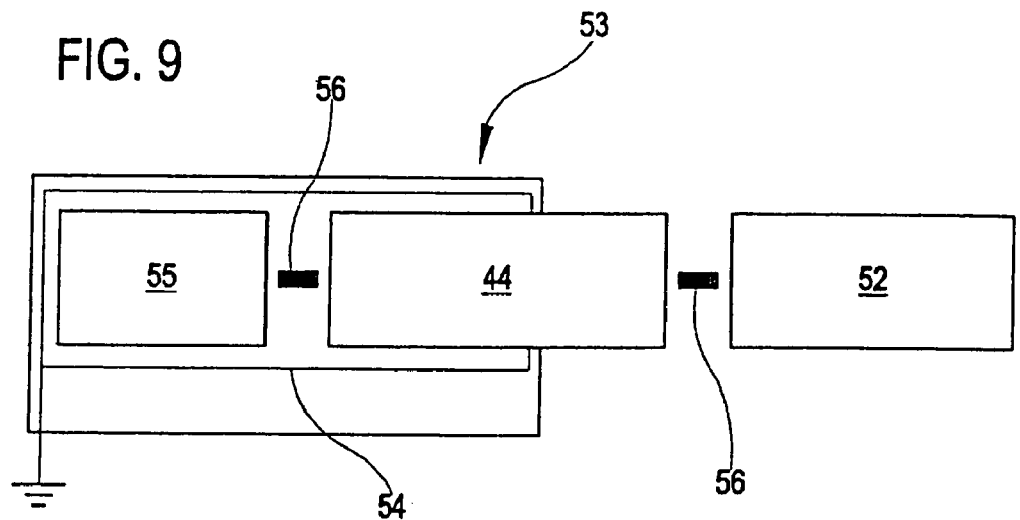
FIG. 9 is a block diagram of the grounding of an extracorporeal circuit according to the present invention.

FIG. 9 shows a block diagram of the electical earthing system of the hydraulic circuit of the apparatus 1. 52 denotes, in its entirety, the disposable part of the dialysis apparatus, which is provided with at least one conductive element in contact with at least one fluid which is transported along at least one tract of the hydraulic circuit of the apparatus. 53 denotes, in its entirety, the fixed part of the dialysis apparatus which comprises the support element 44, which, as mentioned, functions as a mechanical fastening and as an electrical contact for the conductive element of the disposable part. 54 denotes the machine body 54 of the machine, which is equipped with it own galvanic earthing connection 55, of known type. 56 denotes the electrical connections which connect up the various above-mentioned elements among themselves.

Figure 10:
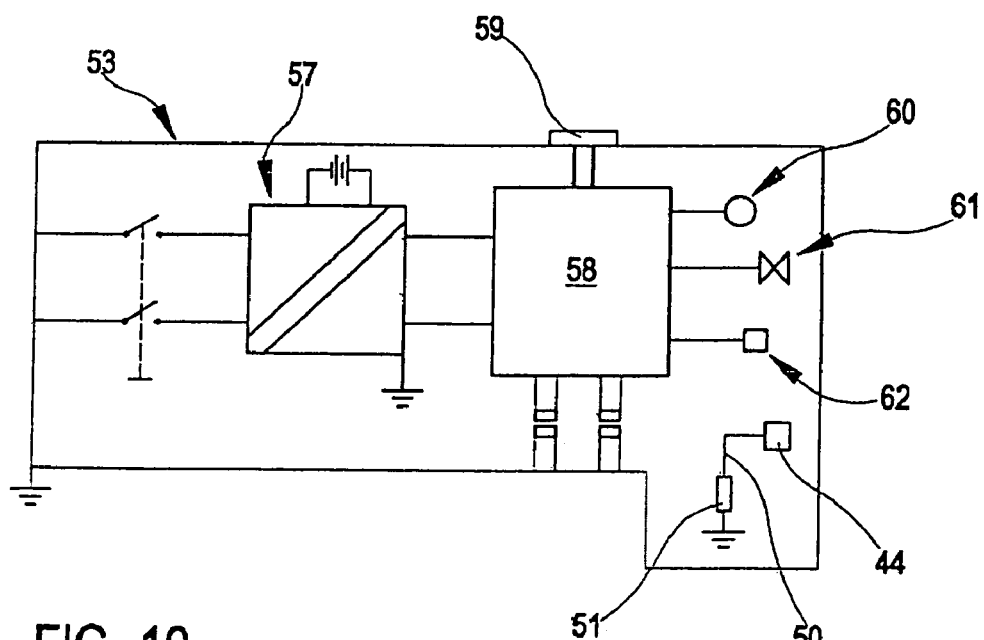
FIG. 10 is a more detailed version of the electrical diagram of FIG. 9.

FIG. 10 is a more detailed electrical diagram: 57 denotes the electric supply, 58 the machine command unit, 59 the operator interface display, 60 the entirety of the peristaltic pumps for circulation of the various fluids (corporeal and medical), 61 the entirety of the control organs for regulation of the various fluid transport lines (clamps, valves, selectors etc.), 62 the totality of the sensors (pressure, blood, air-bubble, any fluid-container weighing sensors there might be, and so on).

During the phase of readying the apparatus for operation, in which the disposable part is associated to the machine, the conductive joint 36 or 36' is pressure-fitted, simply and manually, in the seating constituted by the elastic fastening of the support element 44.

This simple operation makes possible the galvanic grounding connection of the discharge fluid circulating in the drainage line 15b of the dialysis fluid circuit.

Figures from 11 to 13 show the results of some laboratory tests performed to evaluate the effectiveness of the solution proposed in eliminating the ECG artefacts due to the rotation of the peristaltic pumps.

During the tests an apparatus comprising a machine for dialysis treatment was used, such as the one illustrated in FIG. 1, fitted with a disposable integrated module which includes both the blood circuit and the dialysis circuit, and also the dialyzer filter. The dialysis circuit used in the tests is the fluid circuit 15 of FIG. 1, minus branches 21 and 34.

A saline solution (9 g/l) was circulated in the blood circuit, taken from a container and returned to the same container; blood pump flow rate was fixed at 180 ml/min.

Four steel electrodes were immersed in the container, connected by a resistance to terminals L (47 K$\Omega$), R (380 K$\Omega$), F (47 K$\Omega$) and N (47 K$\Omega$) of an electrocardiograph. Terminal. L was unbalanced by introducing, after the resistance, a 400 pF condenser towards the ground. The slight unbalance of the impedance of electrode L transforms the common mode voltage produced by the rotation of the pump into a differential signal which is recorded by the ECG on I.

Before performing the test, the conductivity of the conductive joint 36 was measured. For this purpose, the joint was filled with saline solution (9 g/l) and the electric resistance between the external surface of the joint and the liquid inside was measured. The joint used in the tests had a resistance which varied between 200 KΩ and 2 MΩ.

Figure 11:
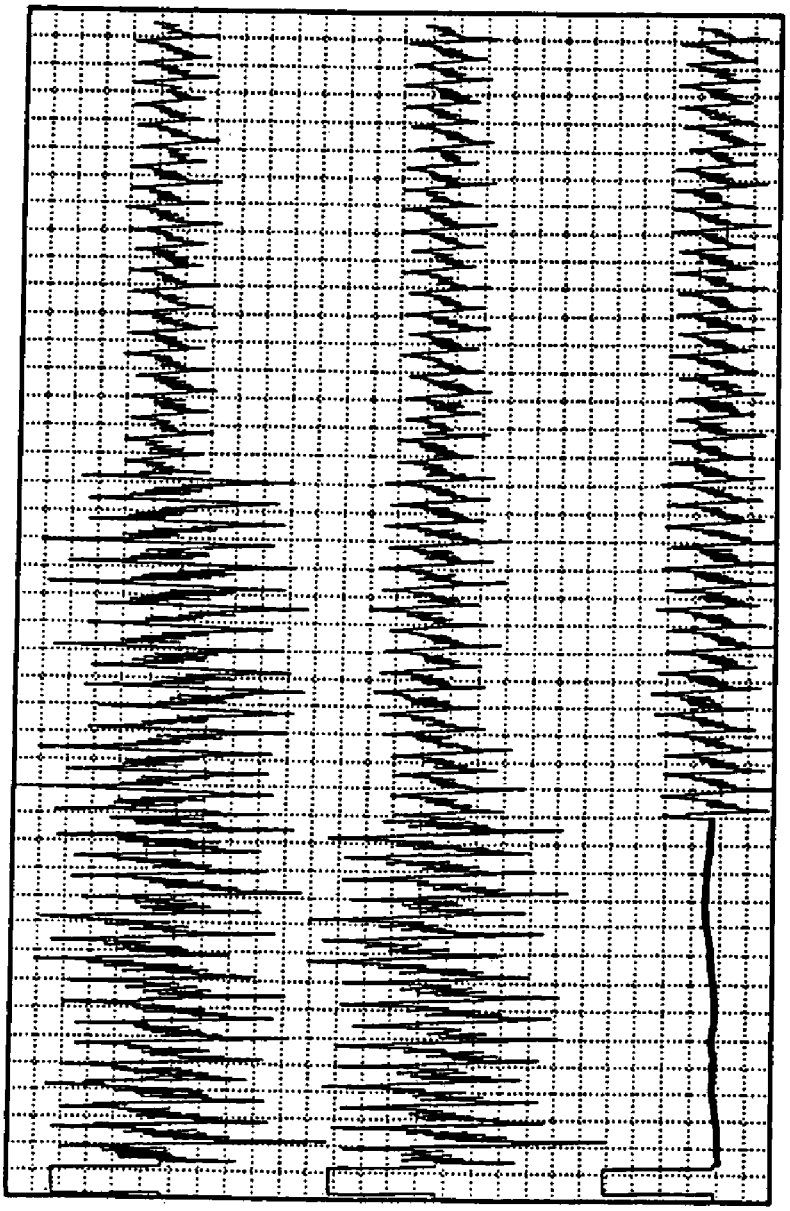
FIG. 11 is a recording of an electrocardiograph applied to a dialysis apparatus during laboratory tests, where the invention is not applied.

FIG. 11, which shows the recording obtained with the conductive joint not grounded, evidences the disturbance produced by the pump rotation (paper speed 25 mm/sec, disturbance synchronous with movement of pump at about 6 c/s). There was disturbance on all cutouts with the exception of no. III, where disturbance is rejected and the impedances of the relative electrodes were exactly balanced. The automatic interpretation of the tracing gives abnormal ECG with atrial fibrillation, abnormal right axial deviation, unspecific intraventricular blockage.

Figure 12:
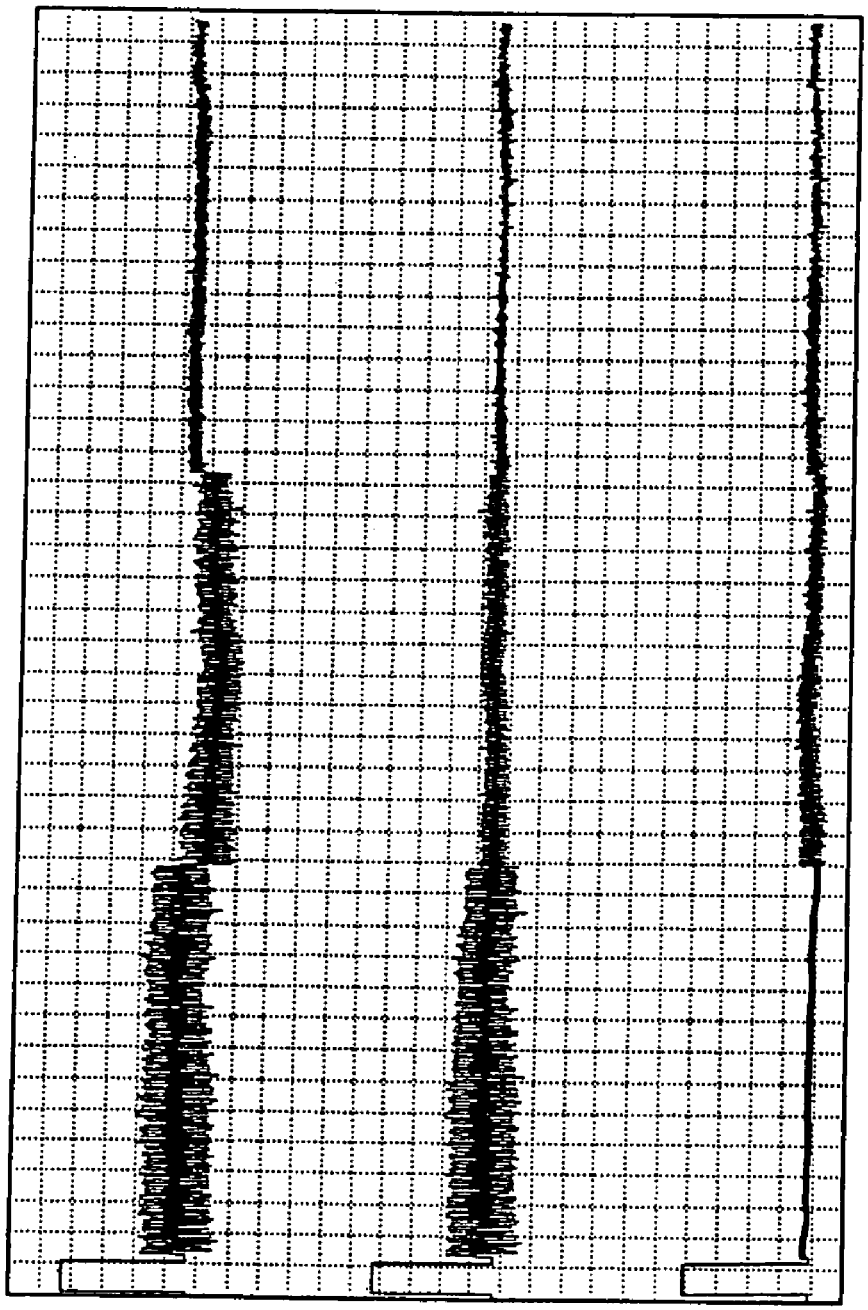
FIG. 12 is an ECG recording applied to the same apparatus as in FIG. 11, where the invention is applied.

FIG. 12 shows the ECG recording of the same test after the conductive joint, positioned on the effluent line immediately downstream of the dialyzer filter, has been galvanically connected to ground. The ground connection consists in connecting the joint by an electric cable to the machine body which in turn is grounded through the supply circuit.

By comparing the recording of FIG. 12 with that of FIG. 11, the ground connection considerably attenuates the disturbance produced by the movement of the blood pump. The automatic response provided by the ECG computer gives atypical ECG (as these were in vitro tests) and declares itself unable to give a complete interpretation.

Figure 13:
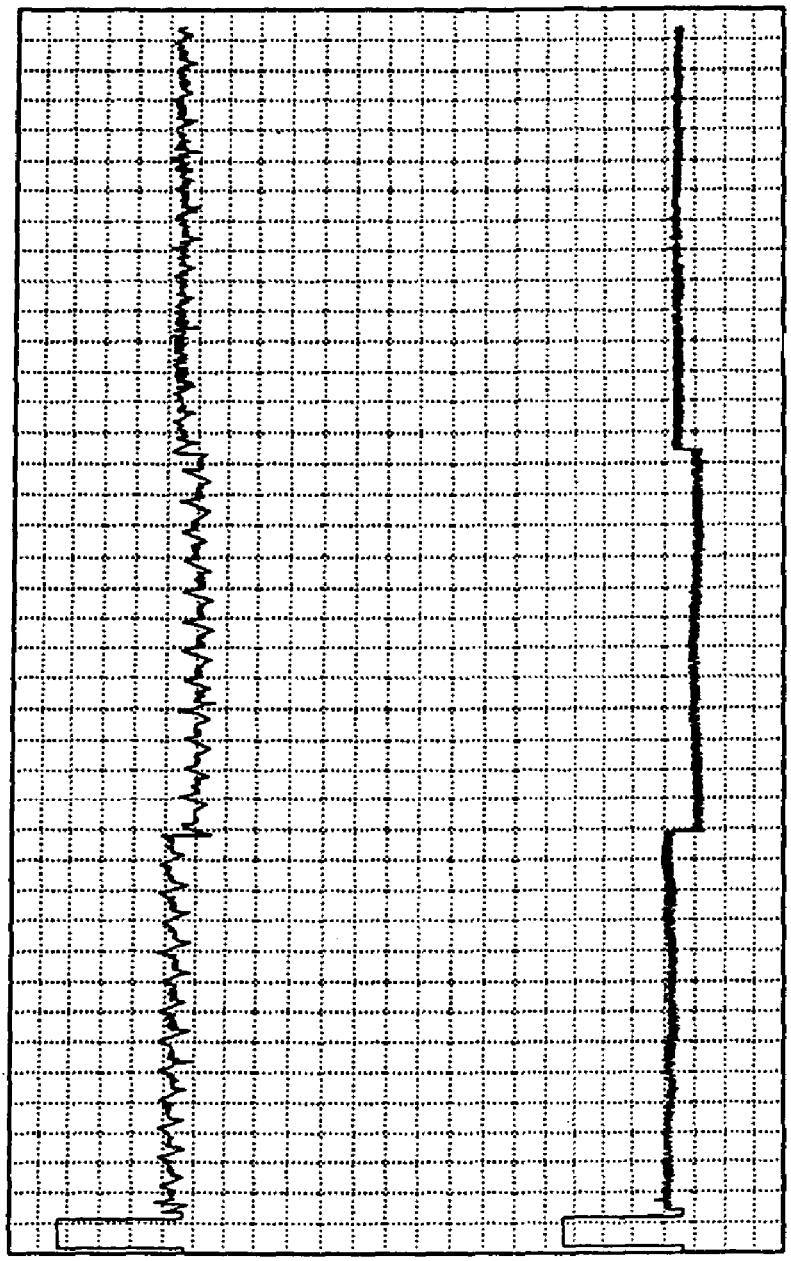
FIG. 13 compares two ECG recordings, taken during laboratory tests; in the first the conductive joint is not earthed, while in the second it is grounded with the interpositioning of a suitable safety grounding resistance.

FIG. 13 compares two test recordings. The top trace relates to a situation in which the conductive joint was not grounded: the automatic interpretation gives abnormal ECG with atrial flutter, epicardiac lesions, possibility of frontal infarct. The bottom trace relates to a situation in which the joint is grounded and in which, along the electric connecting cable between the joint and the body of the machine, a 1.2 MΩ resistance has been positioned. The automatic response describes an atypical ECG, but none of the negative interpretations given for the top tract.

The test result is a demonstration of the elimination of the ECG interference, even when a resistance is put in the ground connection which resistance is sufficient to conserve the requisite of electrical insulation of the machine. The fluid transport line for medical use, comprising the conductive joint 36 or 36', as above described, can be used in the fields various typologies of medical apparatus where ECG interference is a problem. In this specific case the description relates to an apparatus for intensive treatment of acute renal insufficiency: it would be possible however to use the invention in other medical apparatus, such as for example dialysis apparatus for chronic renal insufficiency.

A further example is now described in more detail, of application of the conductive joint in an infusion device, with reference to FIG. 14.

The device comprises:

a source 63 of an infusion liquid;

an infusion line 64 having a first end, an inlet 64a, connected to the source 63 and a second end, an outlet 64b, which is placed in fluid communication, either directly or indirectly, with the vascular system of a patient;

an infusion pump 65, for example a peristaltic pump, operatively associated to the infusion line 64 for circulating the infusion liquid;

a conductive joint 66, made like the joint 36 or 36', predisposed along the infusion line 64 upstream of the pump 65;

a galvanic connection 67 for connecting the conductive joint 66 with an external mass (for example the ground).

The device can further comprises a safety impedance 68, predisposed along the galvanic connection 67, having the function of guaranteeing that the electrical insulation for the patient undergoing the infusion treatment is in conformity with existing safety standards, and a mechanical fastening and electrical contact element, denoted by 69, to which the conductive joint 66 is applied, for example removably.

The infusion line 64 can be connected, directly to a vascular access of the patient, or indirectly to the patient, via an extracorporeal circuit.

In the case of an infusion device too, the material the conductive joint 66 is made of is a polymer which has been made conductive thanks to addition and mixing of carbon black or another known additive. As can be observed, in this case too the conductive joint 66 is located upstream of the peristaltic pump 65, with reference to the infusion. fluid circulation direction.

The electrical contact element 69 destined to engage with the conductive joint 66, which can be once more, for example, an elastic fastening, can be solidly constrained to the pump body of the peristaltic pump 65.

The particular location, before the fluid circulation pump, of the conductive element guarantees reciprocal contact, constantly and in all operative situations, between the transported fluid and the conductive element.

In the illustrated embodiments the transport fluid which is galvanically connected to the outside is, in the first case (FIG. 1) the discharge fluid in the drainage line of a dialyzer filter, and in the second case (FIG. 14) the infusion fluid circulating along an infusion line, simple or cooperating with an extracorporeal blood circuit. Other transport fluids could, however, be galvanically connected to the outside, such as for example blood, circulating in the withdrawal line or the return line of an extracorporeal circuit, or fresh dialyzing fluid, circulating in the supply line of the dialysis chamber of a dialyzer filter, or the pre-infusion or post-infusion liquid of a dialysis circuit.

The invention claimed is:

1. A fluid transport apparatus, comprising:
a fluid transport line for medical use, said fluid transport line comprising at least a first part and a second part, said first and second parts being configured to contact a transported fluid, said second part including a material having an electrical conductivity greater than an electrical conductivity of a material forming said first part, said second part comprising a tubular body made of an electrically conductive material, said tubular body comprising at least one internal surface configured to contact the transported fluid;
at least one pump for circulation of the transported fluid in the fluid transport line;
at least one support element configured to receive said second part in electrical contact therewith, said support element comprising at least a first portion including an electrically conductive material, said first portion being fixed to a bearing structure, said tubular body comprising at least one external surface configured to electrically contact said first portion; and
at least one galvanic connection which connects said support element with an external mass to dissipate electrical charges possibly present in said fluid transport line, said galvanic connection terminating at said first portion.

2. The apparatus of claim 1, wherein said tubular body further comprises a first end having a first connecting zone and a second end having a second connecting zone, said first and second ends being opposite one another.

3. The apparatus of claim 2, wherein said first part includes a first tubular element and a second tubular element, said first and second tubular elements being coupled to said tubular body at said first and second connecting zones.

4. The apparatus of claim 2, wherein said tubular body has an electrical resistance between said internal surface and said external surface, said electrical resistance being comprised between 40 K$\Omega$ and 10 M$\Omega$.

5. The apparatus of claim 4, wherein said electrical resistance is comprised between 200 K$\Omega$ and 2 M$\Omega$.

6. The apparatus of claim 2, wherein said tubular body includes at least one plastic material, said plastic material comprising at least one additive, wherein said additive supplies electric conductivity properties to said tubular body.

7. The apparatus of claim 6, wherein said additive comprises carbon.

8. The apparatus of claim 6, wherein said plastic material comprises PVC.

9. The apparatus of claim 1, wherein said galvanic connection comprises a grounding.

10. The apparatus of claim 1, wherein said galvanic connection comprises at least one electric cable which connects said support element to a machine body, said machine body being in turn connected to ground.

11. The apparatus of claim 1, comprising at least one electrical impedance having a predetermined entity, said electrical impedance being arranged along said galvanic connection.

12. The apparatus of claim 11, wherein the entity of said electrical impedance is greater than 0.1 M$\Omega$.

13. The apparatus of claim 12, wherein the entity of said electrical impedance is equal to or greater than 1.0 M$\Omega$.

14. The apparatus of claim 1, comprising a plurality of electrical impedances having predetermined entities, said plurality of electrical impedances being arranged in parallel along said galvanic connection.

15. The apparatus of claim 1, wherein said support element comprises a second portion, said second portion being dielectric and provided with at least one organ for removable fastening of said tubular body.

16. The apparatus of claim 1, wherein said fluid transport line comprises at least one blood withdrawal line for supplying blood from a patient to a blood treatment device.

17. The apparatus of claim 16, wherein said pump comprises a blood pump for circulation of blood in said blood withdrawal line.

18. The apparatus of claim 1, said fluid transport line comprises at least one blood return line for returning treated blood from a blood treatment device to a patient.

19. The apparatus of claim 1, wherein said fluid transport line comprises at least one drainage line for draining a discharge fluid exiting from a fluid chamber of a blood treatment device, said fluid chamber being separated from a blood chamber by a semi-permeable membrane.

20. The apparatus of claim 19, wherein said pump comprises at least one drainage pump for circulation of discharge fluid in said drainage line.

21. The apparatus of claim 20, wherein said second part is located between said fluid chamber and said drainage pump.

22. The apparatus of claim 1, wherein said fluid transport line comprises an infusion line having a first end configured to be connected to a source of an infusion liquid, and a second end configured to be connected either directly or indirectly with a vascular system of a patient.

23. The apparatus of claim 22, wherein said pump comprises an infusion pump operatively associated to said infusion line for circulating the infusion liquid.

24. The apparatus of claim 1, wherein said fluid transport line comprises at least one supply line for supplying an operative fluid to a fluid chamber of a blood treatment device, said fluid chamber being separated from a blood chamber by a semi-permeable membrane.

25. The apparatus of claim 1, wherein said fluid transport line comprises at least a first infusion line for infusion of a substitution fluid to a blood withdrawal line, said blood withdrawal line being configured to supply blood from a patient to a blood treatment device.

26. The apparatus of claim 1, wherein said fluid transport line comprises at least a second infusion line for infusion of a substitution fluid to a blood return line, said blood return line being configured to return treated blood from a blood treatment device to a patient.

27. The apparatus of claim 1, wherein the material of said second part includes a plastic material, said material having at least one additive such that the material of said second part is electrically conductive.

28. The apparatus of claim 27, wherein said plastic material is elastically deformable.

29. The apparatus of claim 27, wherein said additive increases the rigidity of the material of said second part.

30. The apparatus of claim 27, wherein said additive is carbon and said plastic material is PVC.

* * * * *